(12) United States Patent
Gallucci et al.

(10) Patent No.: US 9,539,370 B2
(45) Date of Patent: Jan. 10, 2017

(54) MEDICAL DEVICE USING SULFONATED NEUTRALIZED POLYMERS WITH REDUCED ADHESION OF BIOLOGICAL FLUIDS

(75) Inventors: Robert R. Gallucci, Mt. Vernon, IN (US); Jan Henk Kamps, Bergen op Zoom (NL); Jon M. Malinoski, Evansville, IN (US); Liming Yu, Clifton Park, NY (US)

(73) Assignee: SABIC Global Technologies, B.V., Bergen op Zoom (NL)

( * ) Notice: Subject to any disclaimer, the term of this patent is extended or adjusted under 35 U.S.C. 154(b) by 422 days.

(21) Appl. No.: 12/546,973

(22) Filed: Aug. 25, 2009

(65) Prior Publication Data

US 2010/0099792 A1 Apr. 22, 2010

Related U.S. Application Data

(60) Provisional application No. 61/106,663, filed on Oct. 20, 2008.

(51) Int. Cl.
*A61L 27/18* (2006.01)
*A61L 31/06* (2006.01)
*A61L 29/06* (2006.01)

(52) U.S. Cl.
CPC ............... *A61L 31/06* (2013.01); *A61L 27/18* (2013.01); *A61L 29/06* (2013.01)

(58) Field of Classification Search
CPC .................................. A61L 27/18; A61L 31/06
USPC ........................................................ 523/105
See application file for complete search history.

(56) References Cited

U.S. PATENT DOCUMENTS

| | | |
|---|---|---|
| 3,959,561 A | 5/1976 | Walles |
| 3,986,997 A | 10/1976 | Clark |
| 4,491,508 A | 1/1985 | Olson et al. |
| 4,615,914 A | 10/1986 | Walles |
| 4,624,870 A | 11/1986 | Anthony |
| 4,861,250 A | 8/1989 | Walles et al. |
| 4,902,493 A | 2/1990 | Walles et al. |
| 4,915,912 A | 4/1990 | Walles et al. |
| 5,030,399 A | 7/1991 | Walles et al. |
| 5,318,856 A | 6/1994 | Misawa et al. |
| 5,346,767 A | 9/1994 | Tilley et al. |
| 5,618,622 A | 4/1997 | Gillberg-Laforce et al. |
| 5,990,188 A | 11/1999 | Patel et al. |
| 6,066,694 A * | 5/2000 | Chisholm et al. .............. 525/67 |
| 6,350,521 B1 | 2/2002 | Chen et al. |
| 6,758,910 B2 | 7/2004 | Schmoyer |
| 2003/0091741 A1 | 5/2003 | Schmoyer |
| 2007/0185221 A1 | 8/2007 | Winter et al. |
| 2008/0171835 A1 | 7/2008 | Sebe et al. |

FOREIGN PATENT DOCUMENTS

| | | |
|---|---|---|
| EP | 0002354 A1 | 6/1979 |
| EP | 0071347 A2 | 2/1983 |
| EP | 0213466 A2 | 3/1987 |

* cited by examiner

*Primary Examiner* — Michael Pepitone
(74) *Attorney, Agent, or Firm* — Richard M. Klein; Fay Sharpe LLP (57) ABSTRACT

A medical article having neutralized sulfonic acid groups on its surface, is disclosed. The article has reduced interaction with biological fluids such as insulin, human growth hormone and human serum albumin.

13 Claims, 1 Drawing Sheet

Fig. 1: Biological Fluid Absoprtion vs. Polycarbonate

Fig. 2: Cation Effects on Bilogical Fluid Absoprtion

MEDICAL DEVICE USING SULFONATED NEUTRALIZED POLYMERS WITH REDUCED ADHESION OF BIOLOGICAL FLUIDS

CROSS REFERENCE TO RELATED APPLICATIONS

This application is a non-provisional application of Provisional Patent Application Ser. No. 61/106,663 filed Oct. 20, 2008, which is incorporated herein by references for all purposes.

BACKGROUND

The present disclosure relates to articles which are functionalized and suitable for use in medical applications. These articles provide surfaces with improved performance.

Polycarbonates are synthetic thermoplastic resins derived from bisphenols and phosgene, or their derivatives. They can be formed from dihydroxy compounds and carbonate diesters, or by ester interchange. Polymerization may be in melt, interfacial, or in nonaqueous solution.

In some circumstances, it may be desirable to modify polymeric surfaces with sulfur containing compounds. This process is usually known as sulfonation. For example, sulfonating a polymeric surface will form a barrier layer with decreased permeability. In addition, sulfonation can be used to make transparent articles that have improved properties.

Sulfonation of a polymeric surface can be achieved in many ways. In some applications, it is necessary to neutralize the sulfonic acid groups generated by the sulfonation process. If unneutralized, the sulfonic acid groups can cause undesired degradation in the end use. For example, transparent sulfonated articles may turn hazy over time when exposed to high temperatures and high relative humidity. Neutralization may be achieved by contacting the sulfonated substrate with a solution containing a base, usually an aqueous solution.

With regard to the base, some polymers, such as vinyl polymers like polyethylene or polystyrene, are not sensitive to degradation caused by the base. Thus, strong bases, such as sodium hydroxide or ammonia, may be used to neutralize those polymers. However, condensation polymers such as polycarbonates, polyester carbonates, and polyesters are sensitive to degradation, especially with strong aqueous bases.

Polymers are used in medical applications where they come into contact with biological fluids such as blood, lymph, and plasma. It is desirable to provide polymers that have improved performance in such environments and applications.

BRIEF DESCRIPTION

Disclosed, in various embodiments, are devices and articles, such as medical devices and articles, which contain neutralized sulfonic acid groups. Such articles have improved properties useful for several applications.

In embodiments, an article is disclosed which comprises a thermoplastic neutralized sulfonated polymer. A surface of the article is functionalized with a sulfonate salt group, the sulfonate salt functionalized surface having at least 35% less adhesion of a biological fluid selected from the group consisting of insulin, human growth hormone, human serum albumin, fibrinogen and mixtures thereof, than a surface that is not functionalized with a sulfonate salt group. As used herein, adhesion means that there is less biological fluid retained on the surface on the article.

The neutralized sulfonated polymer may be selected from the group consisting of polycarbonates, polyesters, polyestercarbonates, polyarylates, and mixtures thereof. In some embodiments, the neutralized sulfonated polymer has repeating units formed from bisphenol-A.

The sulfonate salt may contain a cation selected from the group consisting of sodium, potassium, magnesium, calcium and mixtures thereof. The sulfonate salt may be an aryl sulfonic acid salt. Especially desirable cations are sodium, potassium and magnesium.

In some embodiments, the sulfonate salt functionalized surface has at least 50% less adhesion of a biological fluid than a surface that is not functionalized with a sulfonate salt group. The surface may be sulfonated to a depth of 50 microns or less.

The polymer may have a light transmittance of 70% or greater at a thickness of 3.2 mm, when measured according to ASTM D1003.

The article may be at least 99% neutralized; or to a pH of from about 6 to about 8. The sulfonate salt neutralized surface of the article may have a water contact angle of 25 degrees or less.

The article may be a medical article selected from the group consisting of a blood bowl, syringe, dialysis unit, pump, diaphragm, lens, valve, film, fiber, tube, cover, or handle.

The article may be formed by: molding the article from a polymer to form a polymeric article; contacting the polymeric article with sulfur trioxide to sulfonate a surface of the article; and neutralizing the sulfonated surface with a liquid carboxylate salt solution to form the article having a sulfonate salt functionalized surface.

The surface of the article may be functionalized by a process comprising: providing an article having a non-functionalized surface; drying the article to less than 200 ppm water; contacting the non-functionalized surface of the article with sulfur trioxide to form sulfonic acid groups on the surface of the article; and neutralizing the sulfonic acid groups with an aqueous carboxylate salt solution to form the article having a surface functionalized with a sulfonate salt group, wherein the aqueous solution contains from 10% to 50% by weight of the carboxylate salt.

The surface of the article may alternatively be functionalized by a process comprising: providing an article having a non-functionalized surface; drying the article to less than 200 ppm water; contacting the non-functionalized surface of the article with gaseous sulfur trioxide to form sulfonic acid groups on the surface of the article; and neutralizing the sulfonic acid groups with an aqueous carboxylate salt solution to form the article having a surface functionalized with sulfonate salt groups, wherein the aqueous solution is from 20 to 50% by weight of the carboxylate salt and wherein the carboxylate salt has from one to eight carbon atoms.

The polymer may have a yellowness index of 10 or less, when measured according to ASTM D6290 at a thickness of 3.2 mm; an impact strength of 5 ft-lbs/inch or greater, when measured according to ASTM D256 when measured at a thickness of 0.125 inches (3.2 mm); and/or a haze level of 15% or less at a thickness of 3.2 mm, when measured according to ASTM D1003.

In other embodiments, an article is disclosed which has a surface formed by a neutralized sulfonated polycarbonate polymer. The polymer comprises sulfonic acid groups neutralized by cations, and the polymer has a light transmittance of 70% or greater at a thickness of 3.2 mm, when measured according to ASTM D1003.

In other embodiments, an article comprises a thermoplastic neutralized sulfonated polymer selected from the group consisting of polycarbonates, polyesters, polyestercarbonates, polyarylates, and mixtures thereof, wherein a surface of the article is functionalized with a sulfonate salt group selected from the group consisting of sodium, potassium, magnesium, calcium, and mixtures thereof, the sulfonate salt functionalized surface having at least 35% less adhesion of a biological fluid having a molecular weight of from 5,000 to 400,000 Daltons and selected from the group consisting of insulin, human growth hormone, human serum albumin, fibrinogen and mixtures thereof, than a surface that is not functionalized with a sulfonate salt group.

In other embodiments, an article comprises a thermoplastic neutralized sulfonated polymer. A surface of the article is functionalized with a sulfonate salt group to form a functionalized surface, the sulfonate salt functionalized surface having at least 35% less adhesion of a biological fluid having a molecular weight of from 5,000 to 100,000 Daltons, than a surface that is not functionalized with a sulfonate salt group.

In still other embodiments, an article having a sulfonate salt functionalized surface is disclosed, wherein the surface is functionalized by a process comprising: providing an article comprising a thermoplastic polymer selected from the group consisting of polycarbonates, polyesters, polyestercarbonates, polyarylates and combinations thereof, and wherein the article has a non-functionalized surface; contacting the non-functionalized surface with gaseous sulfur trioxide to form sulfonic acid groups on the surface; and neutralizing the sulfonic acid groups with an aqueous carboxylate salt solution to form the article having a surface functionalized with sulfonate salt groups and wherein the surface has a pH of from about 6 to about 8; wherein the carboxylate salt has from one to six carbon atoms and contains a cation selected from the group consisting of sodium, potassium, magnesium, calcium, and mixtures thereof, and wherein the sulfonate salt functionalized surface has at least 35% less adhesion of a biological fluid having a molecular weight of from 5,000 to 400,000 Daltons and selected from the group consisting of insulin, human growth hormone, human serum albumin, fibrinogen and mixtures thereof, than a surface that is not functionalized with a sulfonate salt group.

These and other non-limiting characteristics are more particularly described below.

DETAILED DESCRIPTION

Numerical values in the specification and claims of this application, particularly as they relate to polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

The present disclosure relates to devices or articles, specifically to medical devices or articles, comprising a neutralized sulfonated polymer. It also relates to devices or articles, such as medical devices or articles, having a surface functionalized with neutralized sulfonic acid groups (i.e. sulfonate salt groups). This functionalization of the article provides a much more polar surface that can be easily wetted and has a low contact angle. This provides a surface which has a reduced adhesion or absorption of biological fluids compared to polymeric surfaces which are less polar and have no ionic groups. Surfaces which have been functionalized with neutralized sulfonic acid groups will also have improved barrier properties, improving resistance to fluids, such as lipids, that often cause cracking in some polymers such as polycarbonates. The functionalized surfaces may also cause less damage to blood cells and reduce adhesion of proteins to the surface. This can be useful in handling blood in applications such as, for example, plasma separation, dialysis, or in heart-lung machines. Such surfaces may have at least 35% less adhesion to biological fluids, such as insulin, human growth hormone, human serum albumin, fibrinogen, and mixtures thereof, than a surface that is not functionalized with a sulfonate salt group. Some surfaces may have at least 50% less adhesion as a result of the functionalization with a sulfonate salt group. These functionalized surfaces may be especially useful for biological fluids having a molecular weight (Mw) from 5,000 to 400,000 Daltons (Da), including biological fluids having a Mw from 5,000 to 100,000 Daltons.

The article is generally formed from a polymeric material or resin. The article can be sulfonated and neutralized after it has been formed, or the article can be formed from a neutralized sulfonated polymer or resin.

In some embodiments, the polymeric material used to form the article is a polycarbonate polymer. Polycarbonate polymers generally contain a repeating structural carbonate unit of the formula (1):

(1)

in which at least 60 percent of the total number of $R^1$ groups are aromatic organic radicals and the balance thereof are aliphatic, alicyclic, or aromatic radicals. In one embodiment, each $R^1$ is an aromatic organic radical, for example a radical of the formula (2):

(2)

wherein each of $A^1$ and $A^2$ is a monocyclic divalent aryl radical and $Y^1$ is a bridging radical having one or two atoms that separate $A^1$ from $A^2$. In an exemplary embodiment, one atom separates $A^1$ from $A^2$. Illustrative non-limiting examples of radicals of this type are —O—, —S—, —S(O)—, —S(O)$_2$—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ may be a hydrocarbon group or a saturated hydrocarbon group such as methylene, cyclohexylidene, or isopropylidene.

Polycarbonates may be produced by the interfacial reaction of dihydroxy compounds having the formula HO—R¹—OH, which includes dihydroxy compounds of formula (3)

wherein $Y^1$, $A^1$ and $A^2$ are as described above. Also included are bisphenol compounds of general formula (4):

wherein $R^a$ and $R^b$ each represent a halogen atom or a monovalent hydrocarbon group and may be the same or different; p and q are each independently integers of 0 to 4; and $X^a$ represents one of the groups of formula (5):

wherein $R^c$ and $R^d$ each independently represent a hydrogen atom or a monovalent linear or cyclic hydrocarbon group and $R^e$ is a divalent hydrocarbon group.

In an embodiment, a heteroatom-containing cyclic alkylidene group comprises at least one heteroatom with a valency of 2 or greater, and at least two carbon atoms. Heteroatoms for use in the heteroatom-containing cyclic alkylidene group include —O—, —S—, and —N(Z)—, where Z is a substituent group selected from hydrogen, hydroxy, $C_{1-12}$ alkyl, $C_{1-12}$ alkoxy, or $C_{1-12}$ acyl. Where present, the cyclic alkylidene group or heteroatom-containing cyclic alkylidene group may have 3 to 20 atoms, and may be a single saturated or unsaturated ring, or fused polycyclic ring system wherein the fused rings are saturated, unsaturated, or aromatic.

Other bisphenols containing substituted or unsubstituted cyclohexane units can be used, for example bisphenols of formula (6):

wherein each $R^f$ is independently hydrogen, $C_{1-12}$ alkyl, or halogen; and each $R^g$ is independently hydrogen or $C_{1-12}$ alkyl. The substituents may be aliphatic or aromatic, straight chain, cyclic, bicyclic, branched, saturated, or unsaturated. Such cyclohexane-containing bisphenols, for example the reaction product of two moles of a phenol with one mole of a hydrogenated isophorone, are useful for making polycarbonate polymers with high glass transition temperatures and high heat distortion temperatures.

Polycarbonate copolymers are also contemplated for use in the instant processes. A specific type of copolymer is a polyester carbonate, also known as a polyester-polycarbonate. Such copolymers further contain, in addition to recurring carbonate chain units of the formula (1), repeating units of formula (7):

wherein $R^2$ is a divalent group derived from a dihydroxy compound, and may be, for example, a $C_{2-10}$ alkylene group, a $C_{6-20}$ alicyclic group, a $C_{6-20}$ aromatic group or a polyoxyalkylene group in which the alkylene groups contain 2 to about 6 carbon atoms, specifically 2, 3, or 4 carbon atoms; and T divalent group derived from a dicarboxylic acid, and may be, for example, a $C_{2-10}$ alkylene group, a $C_{6-20}$ alicyclic group, a $C_{6-20}$ alkyl aromatic group, or a $C_{6-20}$ aromatic group.

In an embodiment, $R^2$ is a $C_{2-30}$ alkylene group having a straight chain, branched chain, or cyclic (including polycyclic) structure. In another embodiment, $R^2$ is derived from an aromatic dihydroxy compound of formula (4) above. In another embodiment, $R^2$ is derived from an aromatic dihydroxy compound.

Examples of aromatic dicarboxylic acids that may be used to prepare the polyester units include isophthalic or terephthalic acid, 1,2-di(p-carboxyphenyl)ethane, 4,4'-dicarboxydiphenyl ether, 4,4'-bisbenzoic acid, and combinations comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or combinations thereof. A specific dicarboxylic acid comprises a combination of isophthalic acid and terephthalic acid wherein the weight ratio of isophthalic acid to terephthalic acid is about 91:9 to about 2:98. In another specific embodiment, $R^2$ is a $C_{2-6}$ alkylene group and T is p-phenylene, m-phenylene, naphthalene, a divalent cycloaliphatic group, or a combination thereof. This class of polyester includes the poly(alkylene terephthalates).

It is possible to make a branched polyester-polycarbonate by incorporating a branching agent, for example, a glycol having three or more hydroxyl groups or a trifunctional or multifunctional carboxylic acid. Furthermore, it is sometimes desirable to have various concentrations of acid and hydroxyl end groups on the polyester, depending on the ultimate end use of the composition.

Useful polyesters may include aromatic polyesters, poly (alkylene esters) including poly(alkylene arylates), and poly (cycloalkylene diesters). Aromatic polyesters may have a polyester structure according to formula (7), wherein D and T are each aromatic groups as described hereinabove. In an embodiment, useful aromatic polyesters may include, for example, poly(isophthalate-terephthalate-resorcinol) esters, poly(isophthalate-terephthalate-bisphenol-A) esters, poly [(isophthalate-terephthalate-resorcinol) ester-co-(isophthalate-terephthalate-bisphenol-A)] ester, or a combination comprising at least one of these. Also contemplated are aromatic polyesters with a minor amount, e.g., about 0.5% by weight to about 10% by weight, based on the total weight of the polyester, of units derived from an aliphatic diacid and/or an aliphatic polyol to make copolyesters. Poly(alkylene arylates) may have a polyester structure according to formula (7), wherein T comprises groups derived from aromatic dicarboxylates, cycloaliphatic dicarboxylic acids, or derivatives thereof. Examples of specifically useful T groups include 1,2-, 1,3-, and 1,4-phenylene; 1,4- and 1,5-naphthylenes; cis- or trans-1,4-cyclohexylene; and the like. Specifically, where T is 1,4-phenylene, the poly(alkylene arylate) is a poly(alkylene terephthalate). In addition, for poly(alkylene arylate), specifically useful alkylene groups D include, for example, ethylene, 1,4-butylene, and bis-(alkylene-disubstituted cyclohexane) including cis- and/or trans-1,4-(cyclohexylene)dimethylene. Examples of poly(alkylene terephthalates) include poly(ethylene terephthalate) (PET), poly(1,4-butylene terephthalate) (PBT), and poly (propylene terephthalate) (PPT). Also useful are poly(alkylene naphthoates), such as poly(ethylene naphthanoate) (PEN), and poly(butylene naphthanoate) (PBN). A useful poly(cycloalkylene diester) is poly(cyclohexanedimethylene terephthalate) (PCT). Combinations comprising at least one of the foregoing polyesters may also be used.

Copolymers comprising alkylene terephthalate repeating ester units with other ester groups may also be useful. Useful ester units may include different alkylene terephthalate units, which can be present in the polymer chain as individual units, or as blocks of poly(alkylene terephthalates). Specific examples of such copolymers include poly(cyclohexanedimethylene terephthalate)-co-poly(ethylene terephthalate), abbreviated as PETG where the polymer comprises greater than or equal to 50 mol % of poly (ethylene terephthalate), and abbreviated as PCTG where the polymer comprises greater than 50 mol % of poly(1,4-cyclohexanedimethylene terephthalate).

Poly(cycloalkylene diester)s may also include poly(alkylene cyclohexanedicarboxylate)s. Of these, a specific example is poly(1,4-cyclohexane-dimethanol-1,4-cyclohexanedicarboxylate) (PCCD), having recurring units of formula (8):

(8)

wherein, as described using formula (7), $R^2$ is a 1,4-cyclohexanedimethylene group derived from 1,4-cyclohexanedimethanol, and T is a cyclohexane ring derived from cyclohexanedicarboxylate or a chemical equivalent thereof, and may comprise the cis-isomer, the trans-isomer, or a combination comprising at least one of the foregoing isomers.

Another type of polycarbonate copolymer is a polysiloxane-polycarbonate copolymer. The polysiloxane (also referred to herein as "polydiorganosiloxane") blocks of the copolymer comprise repeating siloxane units (also referred to herein as "diorganosiloxane units") of formula (9):

(9)

wherein each occurrence of R is same or different, and is a $C_{1-13}$ monovalent organic radical. For example, R may independently be a $C_{1-13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{14}$ aryl group, $C_6$-$C_{10}$ aryloxy group, $C_7$-$C_{13}$ arylalkyl group, $C_7$-$C_{13}$ arylalkoxy group, $C_7$-$C_{13}$ alkylaryl group, or $C_7$-$C_{13}$ alkylaryloxy group. The foregoing groups may be fully or partially halogenated with fluorine, chlorine, bromine, or iodine, or a combination thereof. Combinations of the foregoing R groups may be used in the same copolymer.

The value of D in formula (9) may vary widely depending on the type and relative amount of each component in the polymer, the desired properties of the polymer, and like considerations. Generally, D may have an average value of 2 to 1,000, specifically 2 to 500, and more specifically 5 to 100. In one embodiment, D has an average value of 10 to 75, and in still another embodiment, D has an average value of 30 to 45. The phrase "average value" is used to indicate that various siloxane blocks of siloxane units in the polycarbonate-polysiloxane (PC—Si) copolymer may have different lengths.

In some embodiments, the siloxane unit may be derived from structural units of formula (10):

(10)

wherein D is as defined above; each R may independently be the same or different, and is as defined above; and each Ar may independently be the same or different, and is a substituted or unsubstituted $C_6$-$C_{30}$ arylene radical, wherein the bonds are directly connected to an aromatic moiety. Useful Ar groups in formula (10) may be derived from a $C_6$-$C_{30}$ dihydroxyarylene compound, for example a dihydroxyarylene compound of formula (3), (4), or (6) above. Combinations comprising at least one of the foregoing dihydroxyarylene compounds may also be used. Specific examples of dihydroxyarylene compounds are 1,1-bis(4-hydroxyphenyl) methane, 1,1-bis(4-hydroxyphenyl)ethane, 2,2-bis(4-hydroxyphenyl) propane, 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxyphenyl) cyclohexane, bis(4-hydroxyphenyl sulphide), and 1,1-bis(4-hydroxy-t-butylphenyl) propane. Combinations comprising at least one of the foregoing dihydroxy compounds may also be used.

Units of formula (10) may be derived from the corresponding dihydroxy compound of formula (11):

(11)

wherein R, Ar, and D are as described above. Compounds of formula (11) may be obtained by the reaction of a dihydroxyarylene compound with, for example, an alpha, omega-bisacetoxypolydiorganosiloxane under phase transfer conditions.

In other embodiments, the siloxane unit may be derived from structural units of formula (12):

(12)

wherein R and D are as described above, and each occurrence of $R^4$ is independently a divalent $C_1$-$C_{30}$ alkylene, and wherein the polymerized polysiloxane unit is the reaction residue of its corresponding dihydroxy compound.

In other embodiments, the siloxane unit may be derived from structural units of formula (13):

(13)

wherein R and D are as defined above. Each $R^5$ in formula (13) is independently a divalent $C_2$-$C_8$ aliphatic group. Each M in formula (13) may be the same or different, and may be a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ arylalkyl, $C_7$-$C_{12}$ arylalkoxy, $C_7$-$C_{12}$ alkylaryl, or $C_7$-$C_{12}$ alkylaryloxy, wherein each n is independently 0, 1, 2, 3, or 4.

In one embodiment, M is bromo or chloro, an alkyl group such as methyl, ethyl, or propyl, an alkoxy group such as methoxy, ethoxy, or propoxy, or an aryl group such as phenyl, chlorophenyl, or tolyl; $R^5$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In another embodiment, R is methyl, or a mixture of methyl and trifluoropropyl, or a mixture of methyl and phenyl. In still another embodiment, M is methoxy, n is one, $R^5$ is a divalent $C_1$-$C_3$ aliphatic group, and R is methyl.

Units of formula (13) may be derived from the corresponding dihydroxy polydiorganosiloxane (14):

(14)

wherein R, D, M, $R^5$, and n are as described above. Such dihydroxy polysiloxanes can be made by effecting a platinum catalyzed addition between a siloxane hydride of formula (15):

(15)

wherein R and D are as previously defined, and an aliphatically unsaturated monohydric phenol. Useful aliphatically unsaturated monohydric phenols included, for example, eugenol, 2-allylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl-4-propylphenol, 2-allyl-4,6-dimethylphenol, 2-allyl-4-bromo-6-methylphenol, 2-allyl-6-methoxy-4-methylphenol and 2-allyl-4,6-dimethylphenol. Mixtures comprising at least one of the foregoing may also be used.

Polycarbonates and copolymers may be made by processes such as interfacial polymerization, melt polymerization, melt-process condensation, solution phase condensation, and transesterification polymerization. Although the reaction conditions for interfacial polymerization may vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a catalyst such as triethylamine or a phase transfer catalyst, under controlled pH conditions, e.g., about 8 to about 10. The most commonly used water immiscible solvents include methylene chloride, 1,2-dichloroethane, chlorobenzene, toluene, and the like.

Carbonate precursors include, for example, a carbonyl halide such as carbonyl bromide or carbonyl chloride, or a haloformate such as a bishaloformates of a dihydric phenol (e.g., the bischloroformates of bisphenol-A, hydroquinone, or the like) or a glycol (e.g., the bishaloformate of ethylene glycol, neopentyl glycol, polyethylene glycol, or the like). Combinations comprising at least one of the foregoing types of carbonate precursors may also be used. In an exemplary embodiment, an interfacial polymerization reaction to form carbonate linkages uses phosgene as a carbonate precursor, and is referred to as a phosgenation reaction.

Among the phase transfer catalysts that may be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. An effective amount of a phase transfer catalyst may be about 0.1% by weight to about 10%, optionally about 0.5% by weight to about 2%, by weight based on the weight of bisphenol in the phosgenation mixture.

Branched polycarbonate blocks may be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl) phenol), 4-chloroformyl phthalic anhydride, trimesic acid, and benzophenone tetracarboxylic acid. The branching agents may be added at a level of about 0.05% by weight to about 2.0% by weight. Mixtures comprising linear polycarbonates and branched polycarbonates may be used.

Polyarylates may also be used to form the article having neutralized sulfonic acid groups. Polyarylates are formed from repeating units of formula (7) above, where $R^2$ and T are independently aromatic groups or alkyl aromatic groups. Both $R^2$ and T have at least six carbon atoms and can be the same or different. An exemplary polyarylate is formed from a mixture of isophthalic acid, terephthalic acid, and bisphenol-A. Polyarylates contain primarily aryl ester linkages.

Polyesters may also be used to form the article. Polyesters are formed from repeating units of formula (7) as described above.

Other suitable polymers for forming the article may be selected from the group consisting of polycarbonates, polyesters, polyestercarbonates, polyarylates, and mixtures thereof. Some exemplary polymers include polyethylene terephthalate (PET), polycarbonate polyester blends available as XYLEX® from SABIC Innovative Plastics, copolyester ethers available as ECDEL®, and copolyesters available as SPECTAR™ (PETG) and TRITAN®, all from Eastman Chemical Company.

In specific embodiments, the polymer used to form the article is derived from a dihydroxy compound having the structure of Formula (I):

Formula (I)

wherein $R_1$ through $R_8$ are each independently selected from hydrogen, halogen, nitro, cyano, $C_1$-$C_{20}$ alkyl, $C_4$-$C_{20}$ cycloalkyl, and $C_6$-$C_{20}$ aryl; and A is selected from a bond, —O—, —S—, —SO$_2$—, $C_1$-$C_{12}$ alkyl, $C_6$-$C_{20}$ aromatic, and $C_6$-$C_{20}$ cycloaliphatic.

In specific embodiments, the dihydroxy compound of Formula (I) is 2,2-bis(4-hydroxyphenyl) propane (i.e. bisphenol-A or BPA). Other illustrative compounds of Formula (I) include:

2,2-bis(3-bromo-4-hydroxyphenyl)propane;
2,2-bis(4-hydroxy-3-methylphenyl)propane;
2,2-bis(4-hydroxy-3-isopropylphenyl)propane;
2,2-bis(3-t-butyl-4-hydroxyphenyl)propane;
2,2-bis(3-phenyl-4-hydroxyphenyl)propane;
2,2-bis(3,5-dichloro-4-hydroxyphenyl)propane;
1,1-bis(4-hydroxyphenyl)cyclohexane;
1,1-bis(3-chloro-4-hydroxyphenyl)-3,3,5-trimethylcyclohexane;
4,4'dihydroxy-1,1-biphenyl;
4,4'-dihydroxy-3,3'-dimethyl-1,1-biphenyl;
4,4'-dihydroxy-3,3'-dioctyl-1,1-biphenyl;
4,4'-dihydroxydiphenylether;
4,4'-dihydroxydiphenylthioether; and
1,3-bis(2-(4-hydroxyphenyl)-2-propyl)benzene.

In other embodiments, the polymer used to form the article has repeating units formed from a dihydroisophorone bisphenol or an isoindolone bisphenol.

An example of an isoindolinone bisphenol is shown below as Formula (II):

Formula (II)

wherein $R^3$ and $R^5$ are each independently a halogen, a $C_{1-10}$ alkyl group, alkoxy or a $C_{6-20}$ aryl group; $R^4$ is a $C_{1-6}$ alkyl, a $C_{6-20}$ aryl group, phenyl, or phenyl substituted with up to five halogens, sulfone, alkoxy, or $C_{1-10}$ alkyl groups; and c is, for each $R^3$ and $R^5$, independently an integer from 0 to 4.

An example of a dihydroisophorone bisphenol is shown below as Formula (III):

Formula (III)

The article or polymer may be sulfonated by any process known in the art. For example, the processes disclosed in U.S. Pat. Nos. 5,030,399; 4,915,912; 4,902,493; 4,861,250; 4,615,914; or 3,959,561 may be appropriate. The disclosure of these patents is hereby fully incorporated by reference. For example, the polymer or article may be sulfonated by exposure to sulfur trioxide. Sulfur trioxide will interact with the surface to not only chemically react with it, but also to clean and sterilize it. Sulfur trioxide removes low molecular weight polymer impurities as well as other processing aids which may remain on the surface from earlier polymerization procedures. Sulfur trioxide will also combine with water in the cells of any bacteria present on the surface of the polymer or article to produce sulfuric acid, which destroys the cell membranes of the bacteria. Sulfur trioxide will also react with the polymer to provide sulfonic acid groups, forming a sulfonated polymer or sulfonated article. Additionally, articles with hollow cavities may be sulfonated by the methods described by U.S. Pat. No. 6,758,910, which is fully incorporated by reference herein.

The gas source used is typically an on-site gas generator. The term "on-site gas generator" as used herein means that the gas generator is located at the same location as where the sulfonation is performed such that the sulfur-containing gas is used on demand as it is generated. Any suitable generator that generates a sulfur-containing gas is utilized. Examples include, but are not limited to, sulfur trioxide generators that use a chemical feed stock selected from the group consisting of raw or liquid sulfur, processed sulfur, sulfur dioxide, liquid sulfur dioxide, sulfur trioxide, sulfuric acid and mixtures thereof.

Virtually any means that generates a sulfur-containing compound capable of sulfonating an article may be used in accordance with this disclosure. In one variation, the gas generator system is a sulfur trioxide generator which utilizes molten sulfur transferred from a storage tank into a refractory-lined vessel. In another variation, the sulfur burns in the ambient air conditions to form a gaseous sulfur dioxide/air mixture. This mixture may then flow into a multi-stage catalytic converter where conversion of the sulfur dioxide to sulfur trioxide is extremely efficient. The catalytic converter can be made of vanadium oxide, although other suitable catalytic materials are also contemplated. A useful on-site generator is one which is produced and sold by Chemithon Corporation of Seattle, Wash. Another system that is contemplated includes a liquid sulfur dioxide system which may be utilized where liquid sulfur dioxide is vaporized in a heated tank and mixed with heated air to form a gaseous sulfur dioxide/air mixture. Like the sulfur burning systems, this mixture also flows into a multi-stage catalytic converter where the sulfur dioxide catalytically oxidizes to sulfur trioxide. In yet another variation suitable for smaller applications, the gas generator is of a design that utilizes a sulfuric acid system in which a sulfuric acid-containing composition is transferred into a vaporizer and mixed with heated air to form the sulfur-containing gas. In one variation, the sulfuric acid-containing composition comprises a liquid. In another variation, the sulfuric acid-containing composition comprises fuming sulfuric acid.

Typically, the sulfonating process forms a sulfonated layer onto, or incorporated into, a polymeric article which is made of a sulfonatable material. Moreover, the sulfonation may provide impermeability to various oleophilic materials such as gasoline and other solvents. In addition to the barrier and solvent resistance improvements, sulfonating also provides other properties, including antistatic and antifog properties, and greater adhesion of paints and other types of coatings. Therefore, such surface sulfonated polymeric materials may also be used as substrates for painting and coating. Some other uses contemplated by the present disclosure include sulfonating containers such as articles like food containers including plastic bottles, cartons, tubs and the like, and plastic substrates to be used in a number of industrial applications which need to be painted and/or coated thereafter. Consequently, the number of uses for a sulfonated surface are many fold.

Although the advantages of the methods disclosed herein are not related to any particular theory, it is hypothesized that during sulfonation, hydrogen atoms and derivatives thereof which are bonded to carbon atoms in the polymers, are replaced by sulfonic acid groups, where they become bonded and form a barrier layer. In one variation, this advantage is realized by using polymeric materials which are sulfonatable by the methods of the present disclosure. Suitable polymeric materials include, but are not limited to: polycarbonates; polyarylates; polyester carbonates; polyesters such as polybutylene terephthalate (PBT), polyethylene terephthalate (PET), polycyclohexylene terephthalate (PCT), and polyethylene naphthalate (PEN); and homopolymers, copolymers, and blends thereof. Polymers with a yellowness index (YI) below 10 at a thickness of 3.2 mm are preferred. In particular embodiments, the neutralized sulfonated polymer has repeating units formed from bisphenol-A.

In some variations of the embodiments disclosed herein, a gaseous phase reactant mixture containing from about 1% to about 20% by volume of sulfur trioxide, and balance dry air will require from approximately 8 minutes to about 15 minutes to sulfonate a polyethylene article in a reactor chamber to a degree of from about 0.1 to about 5,000 micrograms $SO_3/in^2$, at room temperature (25° C.). If an optional in-line heater is used to heat the dry air, the higher temperature will allow for a reduced treatment time to achieve the same degree of sulfonation. It is advantageous to employ a reaction temperature in the range from about 15° C. to about 70° C., and specifically from about 15° C. to about 40° C. The reaction is most advantageously carried out at a pressure from about 0.1 to about 70 psi. Typically, the reaction is carried out at about atmospheric pressure.

In a variation of other embodiments of the present disclosure, the water vapor partial pressure of the reactant gas mixture is minimized to improve the uniformity of the sulfonation. The removal of water from the air supply is accomplished by any conventional methodology for reducing water vapor content. Nitrogen may also be used a gaseous diluent. Examples of such methodology include the utilization of vapor tubes, drying agents and the like. The concentration of water in the dry air is less than about 0.01 volume percent. In a further refinement, the concentration of water in the dry air is less than about 0.001 volume percent. In some instances it is desirable to dry the article before sulfonation, in some instances to less than 500 ppm water, in others to below 200 ppm water. Removal of water prior to sulfonation prevents formation of sulfuric acids that may not be as efficient at sulfonation as $SO_3$ and may case undesired side reactions. In some instances the article should be dried to less than 100 ppm water prior to sulfonation.

As set forth above, the sulfonating gas composition includes a sulfur-containing compound and an optional diluent. Although dry air works as a diluent at room temperature, it is especially useful at an elevated temperature of between about 110° C. and 170° C. In a variation, the sulfur-containing gas composition includes a mole percentage of sulfur within the sulfur-containing gas composition from about 1 percent to about 20 percent. The sulfur which is utilized may be sourced from a chemical feedstock selected from the group consisting of raw sulfur, processed sulfur, sulfur dioxide, liquid sulfur dioxide, sulfuric acid, sulfur trioxide and mixtures thereof. Various gas generating procedures will use various precursors, depending upon the equipment utilized and the desired end result. It should be appreciated that some of the sulfur in the sulfur-containing gas is consumed during the treatment to form the sulfonation treatment layer on the surface of the polymeric article.

In further embodiments, the polymer or article is contacted with sulfur trioxide for 10 minutes or less, specifically or 3 minutes or less, or for 60 seconds or less.

The sulfonated polymer or article is then neutralized with a neutralization mixture. Generally, neutralization occurs immediately after sulfonating, i.e. in less than 15 minutes after sulfonating. The sulfonated polymer or article may be contacted with the neutralization mixture by spraying, by dipping, or other known methods.

In embodiments, the neutralization mixture is a liquid solution containing a carboxylate salt. Degradation of sulfonated condensation polymers may be avoided by using salts of carboxylic acids, or carboxylate salts, as the neutralizing agent. Carboxylic acids and their salts are weaker acids than sulfonic acids and will be protonated by the sulfonic acid groups on the sulfonated polymer, effecting a salt exchange. Sulfonate salts, which will not degrade condensation polymers such as polycarbonates, are left behind chemically bonded to the polymeric surface. In embodiments, the sulfonate salt is an aryl sulfonic acid salt. In other words, the sulfonic acid group is attached to an aryl group of the polymer. The carboxylic acids generated as a result of the salt exchange are in solution, are weaker acids, and will not attack the condensation polymer at temperatures below 100° C. Thus, the use of a strong base to neutralize the sulfonated polymer is avoided. The salt exchange is shown in the following equation:

Polymer-SO$_2$OH+RCOO$^-$X$^+$→Polymer-SO$_3^-$X$^+$+ RCOOH where R is alkyl, aryl, or hydrogen and X$^+$ is generally any cation. Thus, processes for neutralizing the sulfonated polymer generally comprise at least two steps. First, a neutralization mixture is made or provided. The mixture comprises a carboxylate salt. Second, the sulfonated polymer is contacted with the neutralization mixture.

The carboxylate salt may generally be formed from any carboxylic acid or mixture of carboxylic acids. Similarly, the neutralization mixture may comprise a mixture of carboxylate salts or a mixture of carboxylic acid(s) and carboxylate salt(s). In embodiments, the carboxylate salt has the general formula RCOO$^-$X$^+$, where R is alkyl, aryl, or hydrogen and X$^+$ is generally any cation. Here, X$^+$ should be considered to refer to any cation having a positive charge, not only cations having a charge of +1. In more specific embodiments, the carboxylate salt may be a metal carboxylate, especially wherein the metal is an alkaline metal or an alkaline earth metal. Such metal carboxylate salts may have the general formula of RCOO$^-$M$^+$. In specific embodiments, the cation/metal is sodium, potassium, magnesium, calcium, or a mixture thereof. In other embodiments, M is a monovalent, divalent, or trivalent metal cation. The carboxylate salt may also be an ammonium carboxylate salt or a phosphonium carboxylate salt. In further embodiments, the carboxylate salt is a tetraaryl ammonium carboxylate salt, tetraalkyl phosphonium carboxylate salt, or tetraaryl phosphonium carboxylate salt. Generally, alkyl phosphonium or ammonium salts that do not have beta protons are more desirable, due to improved thermal stability. In some embodiments, the carboxylate salt contains no nitrogen atoms or halogen atoms. In other embodiments, the carboxylate salt has from 1 to 6 carbon atoms. It is desirable that such a salt be soluble in water. In some instances, the salt is soluble such that at least 25 grams dissolves in 100 ml water at 23° C. In other instances, it is also desirable to have a salt which does not give off gas when neutralized. Non-limiting examples of such salts include sodium propionate, potassium tartrate, and sodium citrate. Carboxylate salts having from one to eight carbon atoms are most desirable. Carboxylate salts should have from 10 to 50% solubility in water at room temperature. In other instances, from 20 to 50 grams of the carboxylate salt will dissolve in 100 ml water.

Generally, the neutralization mixture is an aqueous solution. In embodiments, the neutralization mixture has a pH of from about 6 to about 8.

In some instances, a solvent or mixture of solvents (besides water) may be useful to allow migration of the carboxylate salt into and out of the surface of an article formed from the sulfonated condensation polymer. This results in neutralization slightly below the surface of the article as well. In some embodiments, the surface is sulfonated to a depth of 50 microns or less. In embodiments, the solvent may be selected from the group consisting of alcohols, ethers, ketones, tetrahydrofuran, aprotic polar solvents, and mixtures thereof. In particular, polyethers known as glymes may be used as solvents. Non-limiting examples of aprotic polar solvents include: N-methyl pyrrolidinone (NMP), dimethyl formamide (DMF), dimethyl acetamide (DMAC), dimethyl sulfoxide (DMSO), trimethyl phosphate and hexamethyl phosphoramide (HMPA). Generally, the mixture of carboxylate salts and solvents should be chosen so as not to damage the surface of the article or impair desired properties such as transparency.

The carboxylate salt may be used in amounts of 15 percent by weight ("wt %") or greater of the neutralization mixture (including the water and any solvent if used). In further embodiments, the carboxylate salt is 25 wt % or greater of the neutralization mixture.

In some instances, neutralization of the sulfonated article may be conducted at a temperature of from about 20° C. to about 90° C. In other instances, neutralization can be achieved at a temperature of from about 30° C. to about 70° C.

A method for determining the amount of sulfonation of a resin-containing article includes determining the amount of sulfur in a test sample after sulfonation. This can be determined by forming a first sulfonating gas composition which comprises a sulfur-containing gaseous compound provided from a gas source. One or more first test samples are contacted with the first sulfonating gas composition. Typically, the test samples comprise a resin which is the same as the article to be sulfonated. The one or more first test samples are then contacted with at least one neutralization composition. The amount of sulfur in the one or more first test samples can be determined by inductively coupled plasma analysis and by X-ray fluorescence. In a variation, the inductively coupled plasma analysis utilizes inductively coupled plasma-atomic emission spectroscopy ("ICP-AES"). In one variation, the amount of sulfur in the one or more first test samples is determined by performing both the ICP-AES and X-ray fluorescence measurements on the same test sample. In another variation, the ICP-AES and X-ray fluorescence measurements are performed on different test samples. A calibration relationship between the amount of sulfur determined by inductively coupled plasma analysis and the amount of sulfur determined by X-ray fluorescence is determined with the amount of sulfur determined by inductively coupled plasma analysis taken as an accurate value.

In a subsequent run, a second sulfonating composition is formed. Similarly, the second sulfonating composition comprises a sulfur-containing gaseous compound formed by the gas source. The article to be sulfonated and one or more second test samples are then contacted with the second sulfonating gas composition. Again, the one or more second test samples comprise a resin which is the same as the resin in the article to be sulfonated. The article and the one or more second test samples are then contacted with at least one neutralization composition. Suitable neutralization compositions include the aqueous carboxylate salt solutions set forth above. After neutralization, the articles may be washed one or more times with water to remove any extra carboxylate salt or any carboxylic acid formed by neutralization of the surface-bound sulfonic acids. The amount of sulfur in the one or more second test samples is then measured by X-ray fluorescence using the previously determined calibration relationship. In a subsequent sulfonation run, either the concentration of sulfur-containing compound in the sulfonating gas composition or the time of sulfonation is adjusted to obtain a predetermined level of sulfur in subsequently sulfonated article(s).

The depth of sulfonation of sulfonate salt functionalized parts can be measured by monitoring sulfur content, or generation of sulfur containing byproducts of the analysis technique, at different depths from the surface of the article using standard surface analyses techniques. Examples of surface analysis techniques are: x-ray photoelectron (XPS)

spectroscopy with ion etching or time of flight secondary mass spectrometry scattering (TOF-SIMS) with ion etching.

The article should be neutralized to a pH from 6 to 8, and in some instances from pH 6.5 to 7.5, to prevent degradation of the polymer or unfavorable interaction with the biological fluids. The article may be at least 99% neutralized after contact with the neutralization mixture, that is, neutralization of the article may essentially be complete neutralization of the sulfonic acid groups. The sulfonic acid groups that are bonded to the surface of the article are neutralized by formation of an alkaline earth or alkaline earth metal salt, such as the sulfonate salt. The pH of an article can be measured by contacting, immersing or filling the article with water and then measuring the resultant pH of the water after equilibration (generally from 5 to 60 minutes).

Methods for determining the extent of neutralization of an article are known in the art. An example of one method is measurement of the pH of the solution of a sulfonated article soaked in water. Titration of the aqueous solution with a base and indicator will show the extent of neutralization of the sulfonated article. An example of another method is to measure the amount of sulfur and metal cation, for example sodium, potassium, calcium or magnesium, in the article by x-ray, plasma or other elemental analysis technique and determine that the sulfur and metal cations are present in equal molar amounts. And a further example of a method for determining the amount of sulfonation of an article is to analyze the article by an infrared spectroscopy technique and determine the disappearance of sulfonic acid absorption after neutralization.

Generally, neutralization does not affect certain properties of the article. In embodiments, the neutralized article has a light transmittance of 70% or greater at 3.2 mm thickness, according to ASTM D1003, including a light transmittance of 80% or greater. Alternatively, the neutralized article has a haze level of 15% or less, including 5% or less, when measured at 3.2 mm thickness according to ASTM D1003. The neutralized article may also have a water contact angle of 25 degrees or less. In other embodiments, the neutralized article has a yellowness index of 10 or less, when measured according to ASTM D6290 at a thickness of 3.2 mm. The neutralized article may also have an impact strength of 5 ft-lbs/inch or greater when measured according to ASTM D256 when measured at a thickness of 0.125 inches (3.2 mm).

The neutralized sulfonated article may generally be of any size or shape. For example, the article may be a blood bowl, syringe, dialysis unit, pump, diaphragm, lens, valve, film, fiber, tube, cover, or handle.

The article may be further coated with a clear coating to improve weathering and increase scratch resistance. The article, or part of the article, may be coated with, for example, a scratch resistant coating as described in U.S. Pat. Nos. 6,350,521; 5,990,188; 5,346,767; 5,318,856; 4,624,870; 4,491,508; or 3,986,997 before or after sulfonation. The coating may only be one side of the article, such as an exterior surface of the article.

The neutralized sulfonated condensation polymer and/or the article may further include other additives which can be incorporated with polymeric compositions, with the proviso that the additives are selected so as not to adversely affect the desired properties of the neutralized sulfonated article. Mixtures of additives may be used. Such additives may be mixed at a suitable time during the mixing of the components for forming the article. Examples of such additives include colorants, antioxidants (e.g. hindered phenols), heat stabilizers (e.g. phosphites or phosphonites), light stabilizers (e.g. benzotriazoles or oxazinones), plasticizers, mold release agents (e.g. low molecular weight polyalphaolefins or aliphatic esters), lubricants, antistatic agents, flame retardants, (e.g. sulfonate salts), and anti-drip agents.

The adhesion of biological fluids to plastic surfaces can be measured by any of the techniques known in the art. For example, in one technique an article is filled, washed with or otherwise exposed to a know amount of biological fluid, or biological fluid solution, for example a protein or hormone, and then after a fixed time, the solution is removed, for example by pouring out (dumping) or vacuuming. The amount of biological fluid remaining in or on the article is measured using a technique such as such as immuno-response assay. The biological fluid adhered to the surface of the article is quantified. In the immuno-response assay technique, the bound biological fluid or protein on the article is capped, or modified, with a horseradish peroxidase (HRP) modified antibody specific for that fluid/protein that binds to the absorbed biological fluid/protein. Any excess HRP-modified antibody is washed away. The article is then exposed to a solution of a compound (substrate) that will be converted by the HRP enzyme to yield a color body. The intensity of the color is proportional the amount of the originally absorbed biological fluid.

Biological fluid measurement of bioassays can be done by many techniques including immunoassay procedures. Immunoassay procedures often use a common measurement principle, such as immunological detection and quantification employing protein specific antibodies. For example, the enzyme-linked immunosorbent assay (ELISA) is a biochemical method for detecting specific proteins alone or in complex mixtures. In one embodiment of ELISA, an unknown amount of protein is affixed or absorbed to a surface, and then a specific modified antibody is washed over the surface so that it can bind to the protein. This antibody is linked to an enzyme, and in the final step a substance is added so that the enzyme can convert the substance to generate some detectable signal. The detectable signal can be the generation of a color body, or in the case of fluorescence ELISA, a phosphor may be generated. The amount of the color body or phosphor will be proportionate to the amount of the biological fluid adhering to the article.

In another embodiment, as used in the examples herein, the immunoassay method was a modified type of ELISA technique. The modified ELISA used only one primary antibody labeled with a HRP enzyme. The biological fluid/protein is allowed to equilibrate with the surface of the article, excess biological fluid is washed away, and the surface is then treated with the HRP labeled antibody for that biological fluid/protein. The HRP antibody biological fluid complex is then exposed to a compound that the HRP can convert to generate a colorimetric response. This technique is relatively simple, sensitive, reliable, and suitable for high throughput measurement of multiple samples at same time. The assay may employ a single primary antibody, which is conjugated with an enzyme, for example HRP. The HRP enzyme can convert a colorless substrate into deep blue product (for example SureBlue Reserve TMB substrate (available from Kirkegaard & Perry Laboratories, Inc.) which contains 3,3', 5,5'-tetramethyl benzidine). The more protein that is on the surface, the more antibody molecules that bond, thereby generating more blue color. In going from target protein to the antibody to the HRP, a ratio of about one to one is retained, that is about one molecule of the HRP antibody is bound per adhered biological fluid/protein. However the final step of color generation by HRP enzyme on the color producing substrate is catalytic, which means signal amplification and sensitivity enhancement, making measurement and quantification of the adsorbed biological fluid/protein easier and more efficient.

Biological fluids that can be assayed in this way are many and varied and include, for example, human serum albumin (HSA), human plasma fibrinogen (FBN), human growth hormone (HGH), human glycoprotein immunoglobulin G (human IgG) and insulin.

The following examples are provided to illustrate the compositions and methods of the present disclosure. The examples are merely illustrative and are not intended to limit devices made in accordance with the disclosure to the materials, conditions, or process parameters set forth therein.

EXAMPLES

Example 1

Two articles, SSPC1 and SSPC2, were made having neutralized sulfonic acid groups on their surface. The articles were an injection-molded row of 8 cylinders capped on one end to form wells. They were ~13 mm deep by ~7 mm wide, attached on their sides, with 8 wells per part (article).

It is desirable to predry the polycarbonate parts (articles) at 110° C. to 150° C. before sulfonation, and predrying was done on the articles in these examples. Moisture content of the polycarbonate articles/parts was below 100 ppm.

SSPC1 was a molded polycarbonate part which was contacted with 10 vol % dry gaseous sulfur trioxide ($SO_3$) in dry air for 5 minutes, neutralized for at least 5 minutes in a ~20 wt % aqueous sodium citrate solution, and then washed several times with deionized water.

SSPC2 was similarly modified, but was contacted with 15 vol % dry $SO_3$ for only 2 minutes, followed by aqueous sodium citrate neutralization and washing.

For a control, an unmodified, non-sulfonated polycarbonate part made from a BPA polycarbonate homopolymer having a melt flow rate of 10.5 grams/10 minutes was used.

Figure 1:
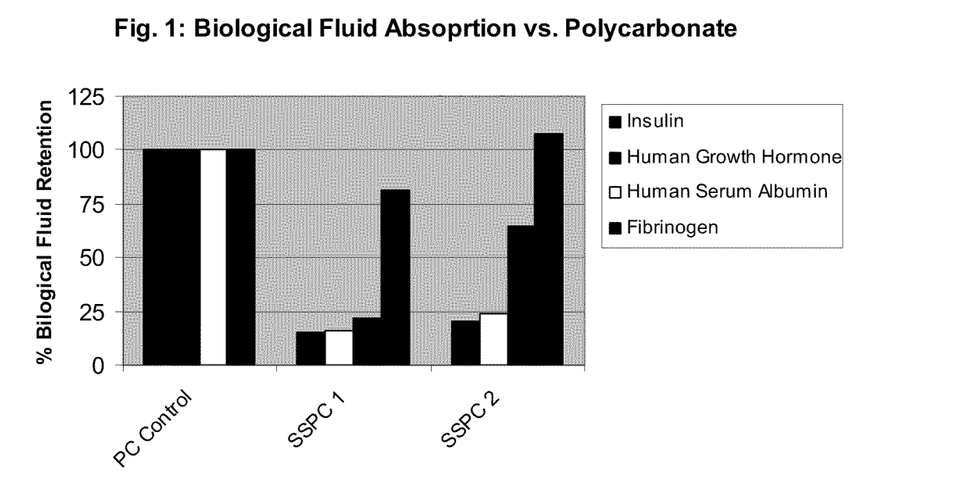
FIGS. 1 and 2 show the relative retention of various biological fluids on an article made from polycarbonate and articles that have been modified with a sulfonate salt functionalized surface.

The parts were then exposed to different biological fluids: Insulin (Mw=5,800 Da), Human Growth Hormone (HGH) (Mw=22,100 Da), Human Serum Albumin (HSA) (Mw=67,000 Da), and Fibrinogen (FBN) (Mw=340,000 Da). The biological fluid was poured into the part, then emptied after about 30 minutes at room temperature. The percentage of absorbed fluid adhering to the plastic part was measured. The results are shown in Table 1 below.

TABLE 1

| % absorption | Insulin | Human Growth Hormone | Human Serum Albumin | Fibrinogen |
|---|---|---|---|---|
| Control | 100.0 | 100.0 | 100.0 | 100.0 |
| SSPC1 | 15.3 | 15.7 | 21.5 | 81.2 |
| SSPC2 | 20.0 | 23.7 | 64.9 | 107.3 |

The amount of absorption by the control was defined to be 100%. SSPC1 and SSPC2 showed strongly reduced adhesion of Insulin and HGH, with absorptions of less than 25%. With HSA, SSPC1 had less than 25% absorption compared to the control while SSPC2 showed 64.9% absorption compared to the control, a 35.1% reduction. Even with fibrinogen, which has complex surface interactions, one of the modified samples (SSPC1) showed reduced adhesion (81.2%) compared to the control. The results showed that the neutralized sulfonated parts had greatly reduced interaction with the biological fluids placed in them, compared to the control

Example 2

Five test well articles were made with neutralized sulfonic acid groups on their surface as described in Example 1. They differed only in the cation used for neutralization.

SSPC3 was a molded polycarbonate part contacted with 10 vol % dry gaseous $SO_3$ in dry air for 5 minutes, neutralized for at least 5 minutes in a ~20 wt % aqueous sodium acetate solution and then washed several times with deionized water.

SSPC4 was similarly modified, but was contacted with 10 vol % dry $SO_3$ for 7 minutes, followed by aqueous sodium acetate neutralization and washing.

SSPC5 was a molded polycarbonate part contacted with 10 vol % dry gaseous $SO_3$ in dry air for 5 minutes, neutralized for at least 5 minutes in a ~20 wt % aqueous potassium acetate solution, and then washed several times with deionized water.

SSPC6 was prepared in the same manner as SSPC5, but used an aqueous magnesium acetate solution for neutralization.

SSPC7 was prepared in the same manner as SSPC5, but used an aqueous calcium acetate solution for neutralization.

All five polycarbonate parts were pre-dried at 110° C. to 120° C. before sulfonation.

The resulting polycarbonate parts all had greater than 80% light transmittance, haze below 5%, and yellowness index (YI) below 10.

For a control, an unmodified, non-sulfonated polycarbonate part made from a polycarbonate homopolymer having a melt flow rate of 10.5 grams/10 minutes was used.

Figure 2:
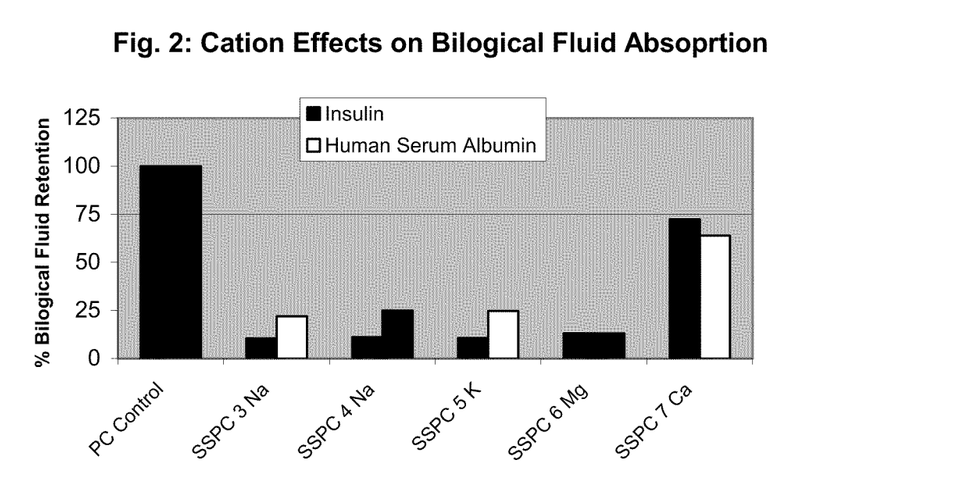

The molded polycarbonate parts were then exposed to Insulin or Human Serum Albumin (HSA). The biological fluid was poured into the part, then emptied. The percentage of absorbed fluid adhering to the plastic part was measured. The results are shown in Table 2 below.

TABLE 2

| % Absorption | Insulin | Human Serum Albumin | Neutralizing Cation |
|---|---|---|---|
| Control | 100.0 | 100.0 | — |
| SSPC3 | 10.6 | 22.0 | Na |
| SSPC4 | 11.2 | 25.0 | Na |
| SSPC5 | 10.7 | 24.8 | K |
| SSPC6 | 13.1 | 13.1 | Mg |
| SSPC7 | 72.4 | 63.9 | Ca |

Again, SSPC3 through SSPC7 all showed strongly reduced adhesion of Insulin and HSA. All of them had less than 75% adhesion, compared to the unmodified control. With Insulin, the sodium, potassium and magnesium sulfonate salts had less than 15% absorption, compared to the control. The calcium sulfonate salt was not as effective as the sodium, potassium and magnesium sulfonate salts in reducing the adhesion, but was still much more effective than the unmodified (non-sulfonated) control.

The procedures used to measure biological fluid adhesion to the articles of the Examples are described below. An aqueous solution of the biological fluid was poured into the part and allowed to sit, and then the fluid was emptied after sitting for about 30 minutes at room temperature. The percentage of absorbed fluid adhering to the plastic part was measured using an immunoassay procedure. Examples of immunoassay procedures for FBN and HSA are detailed below. Similar methods were used for insulin and HGH.

Procedure for Fibrinogen (FBN) adsorption assay. Preparation of stock and working FBN solution: (1): Powdered Fibrinogen was dissolved in 50 mM $NaHCO_3$ buffer (pH 8.3) to a final concentration higher than 1.2 mg/ml. The solution is absorbance at 280 nm was measured, adjusting the volume to make the final concentration exactly 1.2 mg/ml based on the extinction coefficient of 15.1. (2): Aliquot the protein solution in 1 ml/tube and store at −80° C. (3): On the day of the test, thaw the frozen stock tube(s) needed for the experiment(s), dilute in aqueous phosphate buffered solution (PBS) to a final concentration of 300 µg/ml (working solution), and keep on ice until ready to use.

Protein adsorption: (1): Add PBS buffer to a 200 µl plastic test well (the sulfonate salt surface modified article) and equilibrate at room temperature for 15 to 30 minutes. (2): Vacuum away the PBS buffer. (3): Add 70 µl protein working solution to each well of the test material or strips. Three replicates were used for each material. Avoid using the wells at the edge to eliminate any edge effect (from molding, coating, or any other processing). Equilibrate test wells at room temperature for 30 minutes. (4): Remove the protein solution by vacuum or dumping.

Blocking: (1): Add 2% goat serum in PBS 200 µl well, equilibrate at room temperature for 30 minutes. Remove the goat serum solution by vacuum or dumping. (2): Wash the plate with PBS twice using 200 µl for each well for each wash.

Add HRP labeled anti-fibrinogen antibody: (1): A vial of 200 µl antibody from Abcom Co. was mixed with 200 µl of glycerol and stored at −20° C. (2): 2 µl of the stock antibody was mixed with 2 ml of 2% goat serum in PBS (1:1000 dilution). The appropriate amount of 1:1000 diluted solution was further diluted with an equivalent amount of 2% goat serum in PBS to 1:400 (final dilution=1:400,000). This is the working solution and needs to be prepared just prior to using the solution. (3): Add 70 µl antibody working solution to each well and equilibrate at room temperature in a dark area for 1 hour.

Washing: (1): Remove the antibody solution by vacuum or dumping. (2): Wash with 200 µl per well PBS by vacuum or vigorous dumping 5 times.

Color development: (1): Add 100 µl per well of room temperature balanced HRP substrate, equilibrate at room temperature in a dark area for exactly 15 minutes. (2): Add 100 µl per well of a 2M aqueous sulfuric acid HRP stop solution.

Measurement: (1): Transfer 150 µl solution from each well to a new clear bottom 96-well plate. (2): Blow the plate briefly with hot air using a hair dryer. This step helps to remove all the bubbles in the well that may affect readings. (3): Set up the ELISA reader at 450 nm adsorption reading with pre-shaking for 3 seconds. Use a stop solution as the blank. Take a color absorbance reading form the sample.

Procedure for Human Serum Albumin (HSA) adsorption assay. Preparation of stock and working HSA solution: (1): Weigh HSA powder in milligrams and dissolve it in PBS buffer to a final concentration higher than 2 mg/ml. Measure its absorbance at 280 nm using a NanoDrop ND1000 spectrometer and convert to protein concentration using the equation integrated in the instrument. Adjust the volume accordingly to make the protein concentration to be exactly 2 mg/ml. (2): Aliquot the protein solution in 1 ml/tube and store at −80° C. (3): On the day of test, thaw frozen stock tube(s) needed for the experiment(s), dilute in PBS to a final concentration of 20 µg/ml (working solution), and keep on ice before use.

Protein adsorption: (1): Add PBS buffer (200 µl per well) and equilibrate at room temperature for 15 to 30 minutes. (2): Vacuum to remove the PBS buffer. (3) Add 70 µl protein working solution to each well of the test material strips. Three replicates are used for each material. Avoid using the wells at the edge to eliminate any edge effect (from molding, coating, or any other processing). Equilibrate the test wells at room temperature for 30 minutes. (4): Remove the protein solution by vacuum or dumping.

Blocking: (1): Add 2% rabbit serum in PBS (200 µl per test well), equilibrate at room temperature for 30 minutes. Remove the rabbit serum solution by vacuum or dumping. Wash each well twice with 200 µl of phosphate buffer solution (PBS).

Add HRP labeled anti-HSA antibody: (1): A vial of 200 µl antibody from Abcom Co. was mixed with 200 µl of glycerol and stored at −20° C. (2): 2 µl of the stock antibody was mixed with 2 ml of 2% rabbit serum in PBS (1:1000 dilution). The appropriate amount of 1:1000 dilution solution was further diluted with the appropriate amount of 2% rabbit serum in PBS to 1:50 (final dilution=1:50,000) to make the working solution (which needs to be prepared right before using). (3): Add 70 µl antibody working solution to each well and equilibrate at room temperature in a dark area for 1 hour.

Washing: (1): Remove the antibody solution by vacuum or dumping. (2): Wash with 200 µl per well using PBS by vacuum or dumping 5 times.

Color development: (1): Add 100 µl per well of room temperature balanced HRP substrate, equilibrate at room temperature in a dark area for exactly 15 minutes. (2): Add 100 µl per well of a 2M aqueous sulfuric acid HRP stop solution.

Measurement: (1): Transfer 150 µl solution from each well to a new clear bottom 96-well plate. (2): Blow the plate briefly with hot air using a hair dryer. (3): Set up the ELISA reader at 450 nm adsorption reading with pre-shaking for 3 seconds. Use a stop solution as the blank. Take a color absorbance reading form the sample.

The devices, articles, and processes of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. An article comprising a thermoplastic neutralized sulfonated polycarbonate,
    wherein an interior surface of the article is functionalized with a sulfonate salt group containing a cation selected from the group consisting of sodium, potassium, magnesium, calcium, and mixtures thereof, the sulfonate salt functionalized surface having at least 50% less adhesion of a biological fluid having a molecular weight of from 5,000 to 400,000 Daltons and selected from the group consisting of insulin, human growth hormone, human serum albumin, fibrinogen and mixtures thereof, than a surface that is not functionalized with a sulfonate salt group;
    wherein an exterior surface of the article is coated with a clear scratch-resistant coating; and
    wherein the interior surface is not clear coated; and wherein the article is a medical article selected from the group consisting of a blood bowl, syringe, dialysis unit, pump, or tube.

2. The article of claim 1, wherein the sulfonate salt group is an aryl sulfonic acid salt.

3. The article of claim 1, wherein the polycarbonate has a light transmittance of 70% or greater at a thickness of 3.2 mm, when measured according to ASTM D1003.

4. The article of claim 1, wherein the sulfonate salt functionalized surface is sulfonated to a depth of 50 microns or less.

5. The article of claim 1, wherein the sulfonate salt functionalized surface has a water contact angle of 25 degrees or less.

6. The article of claim 1, wherein the article is neutralized to a pH of from about 6 to about 8.

7. The article of claim 1, wherein the article is formed by:
molding the article from a polycarbonate to form a polymeric article;
contacting the polymeric article with sulfur trioxide to sulfonate a surface of the article; and
neutralizing the sulfonated surface with a liquid carboxylate salt solution to form the article having a sulfonate salt functionalized surface.

8. The article of claim 1, wherein the surface of the article is functionalized by a process comprising:
providing the article having a non-functionalized surface;
contacting the surface of the article with sulfur trioxide to form sulfonic acid groups on the surface of the article; and
neutralizing the sulfonic acid groups with an aqueous carboxylate salt solution to form the article having a surface functionalized with a sulfonate salt group, wherein the aqueous solution contains from 10% to 50% by weight of the carboxylate salt.

9. The article of claim 8, wherein the carboxylate salt has a solubility at 23° C. of at least 25 grams of salt per 100 ml water, wherein the carboxylate salt has from one to six carbon atoms and contains a cation selected from the group consisting of sodium, potassium, magnesium, calcium, and mixtures thereof.

10. The article of claim 1, wherein the surface of the article is functionalized by a process comprising:
providing the article having a non-functionalized surface;
drying the article to less than 200 ppm water;
contacting the non-functionalized surface of the article with gaseous sulfur trioxide to form sulfonic acid groups on the surface of the article; and
neutralizing the sulfonic acid groups with an aqueous carboxylate salt solution to form the article having a surface functionalized with sulfonate salt groups, wherein the aqueous solution is from 10 to 50% by weight of the carboxylate salt and wherein the carboxylate salt has from one to eight carbon atoms.

11. The article of claim 1, wherein the polycarbonate has a yellowness index of 10 or less, when measured according to ASTM D6290 at a thickness of 3.2 mm.

12. The article of claim 1, wherein the polycarbonate has an impact strength of 5 ft-lbs/inch or greater, when measured according to ASTM D256 at a thickness of 3.2 mm.

13. The article of claim 1, wherein the polycarbonate has a haze level of 15% or less at a thickness of 3.2 mm, when measured according to ASTM D1003.

* * * * *